United States Patent [19]

Alt

[11] Patent Number: 5,031,614
[45] Date of Patent: Jul. 16, 1991

[54] PACEMAKER RATE CONTROL USING AMPLITUDE AND FREQUENCY OF ACTIVITY SIGNAL

[76] Inventor: Eckhard Alt, Eichendorff Strasse 52, 8012 Ottobrunn, Fed. Rep. of Germany

[21] Appl. No.: 525,768

[22] Filed: May 21, 1990

Related U.S. Application Data

[60] Continuation-in-part of Ser. No. 516,812, Apr. 30, 1990, which is a division of Ser. No. 94,875, Sep. 10, 1987, Pat. No. 4,926,863.

[51] Int. Cl.$^5$ .............................................. A61N 1/00
[52] U.S. Cl. ........................... 128/419 OPG; 128/782
[58] Field of Search ......................... 128/419 PG, 782

[56] References Cited

U.S. PATENT DOCUMENTS

| | | | |
|---|---|---|---|
| 4,428,378 | 1/1984 | Anderson et al. | 128/419 PG |
| 4,686,987 | 8/1987 | Salo et al. | 128/419 PG |
| 4,733,667 | 3/1988 | Olive et al. | 128/419 PG |
| 4,771,780 | 9/1988 | Sholder | 128/782 |

*Primary Examiner*—Francis Jaworski
*Assistant Examiner*—George Manuel
*Attorney, Agent, or Firm*—Leitner, Greene & Christensen

[57] ABSTRACT

A variable rate pacemaker responsive to patient exercise senses physical activity of the patient by motion detection and generates a corresponding electrical signal. The pacemaker circuitry detects maximum and minimum values of the amplitude of the electrical signal in equal intervals of time. These time intervals are selected to be shorter than the shortest possible interval between repetitions or of the cycle representing speed of the physical activity. Only one parameter is calculated, namely the difference in maximum and minimum amplitude within each time interval, to determine both the amplitude of the signal corresponding to intensity of the exercise and, indirectly, the frequency of the signal corresponding to exercise speed and repetition rate, for use in pacemaker rate control. In a specific embodiment, the data of successive time intervals is averaged into data blocks, and a first-in, first-out technique is applied to the averaged data blocks for use in the desired pacing rate control.

31 Claims, 12 Drawing Sheets

FIG. 5a
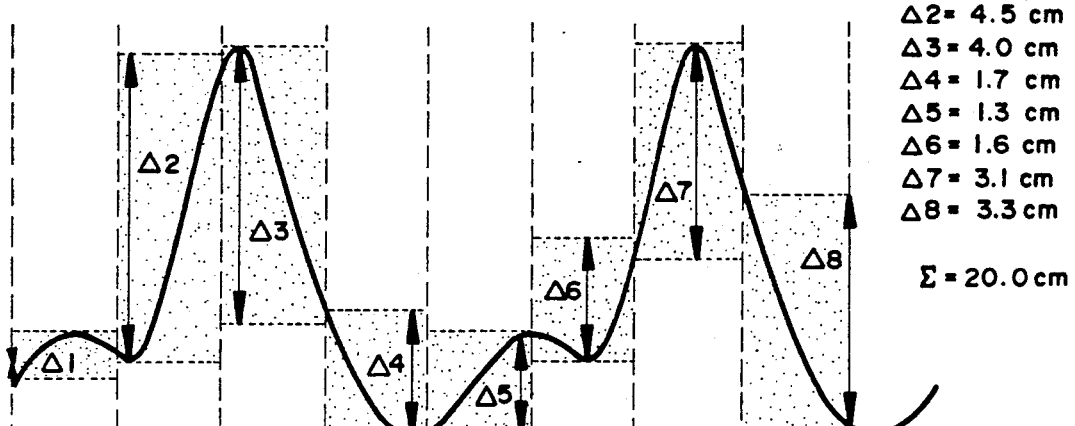
Δ1 = 0.5 cm
Δ2 = 4.5 cm
Δ3 = 4.0 cm
Δ4 = 1.7 cm
Δ5 = 1.3 cm
Δ6 = 1.6 cm
Δ7 = 3.1 cm
Δ8 = 3.3 cm
Σ = 20.0 cm
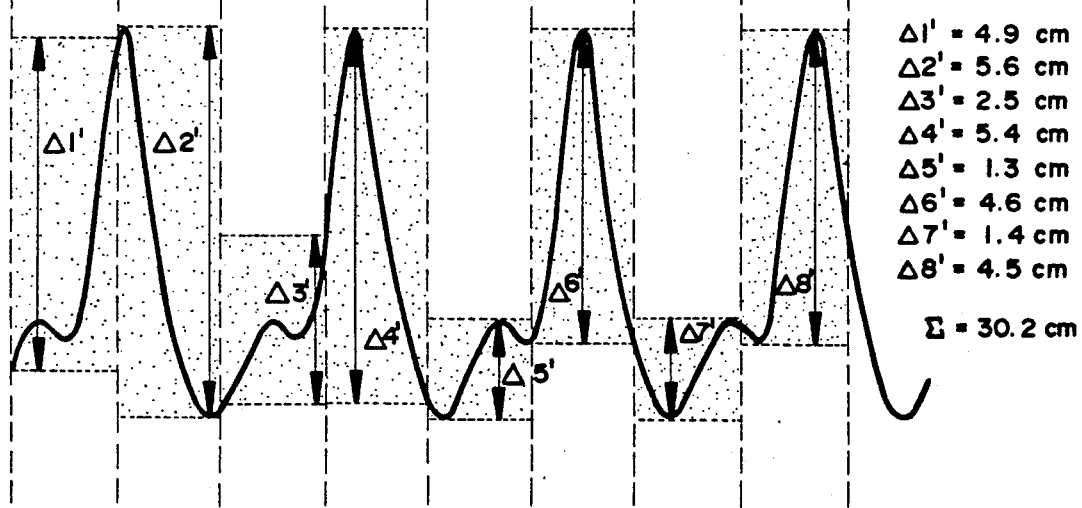
Δ1' = 4.9 cm
Δ2' = 5.6 cm
Δ3' = 2.5 cm
Δ4' = 5.4 cm
Δ5' = 1.3 cm
Δ6' = 4.6 cm
Δ7' = 1.4 cm
Δ8' = 4.5 cm
Σ = 30.2 cm
FIG. 5b

PACEMAKER RATE CONTROL USING AMPLITUDE AND FREQUENCY OF ACTIVITY SIGNAL

CROSS-REFERENCE TO RELATED APPLICATIONS

This application is a continuation-in-part of copending U.S. patent application Ser. No. 07/516,812, filed Apr. 30, 1990 (hereinafter "the '812 application") by the same inventor, the '812 application being a division of copending U.S. patent application Ser. No. 07/094,875 filed Sep. 10, 1987, now U.S. Pat. No. 4,926,863 issued May 22, 1990 (hereinafter "the '863 patent"), each of which is assigned to the same assignee.

BACKGROUND OF THE INVENTION

The present invention relates generally to implantable cardiac pacemakers, and more particularly to a pacemaker in which the stimulation rate is responsive or adaptive to patient exercise as detected by movement or activity.

Since the advent of the artificial implantable cardiac pacemaker, the aims of cardiac pacing have changed from the initial goal of simply providing a lower rate limit to prevent life-threatening asystoly, to the present-day broad objective of improving the overall quality of life of the pacemaker patient. Quality of life, in this context, pertains to the performance of the heart under widely varying metabolic and hemodynamic conditions. Patients with conventional single chamber pacemakers often lack adequate heart rate and cardiac output to sustain more than slight physical exertion, and consequently suffer severe limitations on activity and fitness. For patients with complete AV block and normal sinoatrial node activity, the dual-chamber pacemaker can restore an adequate adaptation of heart rate to exercise; but that solution serves only a relatively small portion of the pacemaker patient population, and such pacemakers are susceptible to disturbances.

As a result, numerous studies have been conducted over the years seeking to uncover parameters which act internal or external to the body for possible use in controlling pacemaker stimulation rate. The goal is to control the heart rate of a pacemaker patient in a manner similar to the intrinsic heart rate of a healthy person with a normal functioning heart, under various conditions of rest and exercise; which is to say, in a physiologically appropriate manner.

Applicant's German Patent No. DE 34 19 439 and related U.S. Pat. No. 4,688,573 (the "'573 patent") disclose techniques for rate responsive pacing which utilize both absolute temperature values and relative temperature changes of the central venous blood of the patient under various physiological conditions, and which utilize separate algorithms defining heart rate as a function of blood temperature for states of rest and exercise, respectively, together with the decision rule for selecting which of the algorithms is appropriate at any given time.

The detection of activity- or motion-induced forces within or on the body by means of a piezoelectric crystal, a microphone or other mechanoelectrical transducer has been used to generate electrical signals to control the rate of an implanted pacemaker. Such techniques have exhibited fast response to the onset of exercise, but various disadvantages including undesirable response to noise disturbances external to the body, such as from nearby operating machinery, or emanating from within the body, such as from coughing, sneezing, laughing, or the like. Accordingly, disturbances unrelated to exercise can affect the heart rate, when accelerometer-type detection is utilized for control of the pacemaker stimulation rate.

The art prior to the invention disclosed in the '875 application teaches that, during patient exercise, the maximum acceleration values detected by an activity-controlled cardiac pacemaker occur in the range of the resonant frequency of the major body compartments such as the thorax and the abdomen, i.e. approximately 10 Hz. See, for example, the Proceedings of the European Symposium on Cardiac Pacing, editorial Grouz, pp. 786 to 790, Madrid, 1985). It was believed, therefore, that the maximum sensitivity should be in the range above 10 Hz (e.g., see also. Biomedizinische Technik. 4. pp. 79 to 84, 1986, and U.S. Pat. No. 4,428,378).

To the contrary, the '863 teaches that the maximum amplitude activity-sensed signals occurring with exercise such as walking, climbing stairs, running and bicycling occur with rhythmical motions of the body, in the low-frequency range below 4 Hz. That application shows that amplitude maxima in the higher-frequency range, above 4 Hz, arise instead from sudden spasmodic movements which do not represent true metabolic exercise. The indicia of the latter movements are readily excluded by limiting detection to only the low-frequency content, which correlates well with the metabolic demand of the body in true exercise. By using the frequency band below 4 Hz, the cardiac pacemaker disclosed in the '875 application reliably generates stimuli at rates adapted to the overall metabolic state of the patient. The stimulation rate of the pacemaker is responsive to the level of physical exertion of the patient, closely corresponding to the heart rate of a normal healthy person under the same conditions of physical exertion. The pacemaker employs an accelerometer (activity or motion sensor) in the form of a microminiature mechanoelectrical converter or transducer of suitably low power consumption, which is adapted either by virtue of its construction or by use of associated filter circuitry to pass signals in a frequency band which is preselected to avoid increased rates of stimulation in response to false indications of exercise.

The '863 patent also teaches that a second sensor may be employed for detecting a parameter complementary to acceleration, for dual sensor confirmation of metabolic state and selective contribution to the pacer's stimulation rate. The "complementary parameter" may be any physiological or other detectable parameter of the body or acting outside the body, whose characteristics of sensitivity and specificity to physical exercise contrast with and enhance the corresponding characteristics of the activity sensor. Such dual sensor pacing avoids a primary disadvantage of previous activity sensing pacers (aside from their reliance on a frequency band generally exceeding 10 Hz), of inability to respond to the instantaneous metabolic level of exercise despite fast response to the onset of exercise. The dual sensor pacing also overcomes the disadvantage of a single parameter sensing pacemaker, using only the central venous blood temperature, for example, which responds slowly to the onset of exercise (although that parameter is quite sensitive to the metabolic level of exercise).

In the frequency range above 4 Hz in general, and above 10 Hz in particular, noise detected in close proximity to operating machinery, or arising from coughing, laughing, sneezing or straining by the patient wearing the prior type of activity-based pacemaker, displays amplitude maxima up to about tenfold the amplitude maxima of signals attributable to true physiological exercise. Thus, the noise signals tend to swamp the activity-induced signals at the higher frequencies. Light knocks upon, bumps against or touching of the pacemaker are picked up as impulse characteristics in the higher-frequency range, but are detected, if at all, with very low amplitudes in the low-frequency range up to 4 Hz. Also, because the duration of the pulse wave deriving from the propagation of the pulse with every heart beat is in the range of about 70 to 120 milliseconds (ms), it has an impulse characteristic with maximum amplitude in the higher-frequency range at about 10 Hz, despite the fact that the heart rate itself is in the range from 60 to 180 beats per minute (bpm) corresponding to a frequency of 1 to 3 Hz.

The invention claimed in the '812 application utilizes the low-frequency spectrum in performing reliable detection of signal amplitude maxima and minima with a relatively low sampling rate, in contrast to the higher rate required if the high-frequency range is selected. The availability and use of a low sampling rate results in a considerable saving of energy, which is an important advantage because implantable pacers have extremely limited energy capacity.

Also, rate control may be achieved with an activity sensing pacemaker as disclosed in the docket '103 application, by using relative changes of amplitude of the processed activity-induced signal, rather than absolute values, for adjusting the stimulation rate. This avoids false triggerings caused by ambient noise. It also make pacing rate increases a function not only of whether a predetermined baseline value is exceeded but the actual rate at that time, so the specific amount of the increase is smaller at the higher rates.

The mechanoelectrical transducer disclosed in the '863 patent is a piezoelectric, piezoresistive or piezocapacitive sensor fabricated in a semiconductor substrate. Indeed the sensor may be integrated with signal processing circuitry in a single silicon chip, by use of conventional semiconductor manufacturing process technology. With appropriate geometrical configuration, the sensor itself provides the desired frequency bandpass characteristics to capture the proper signal, such as by fabricating the transducer in the form of a vibratory cantilever arm of material and length selected to provide it with the desired resonant frequency.

According to the invention of the '812 application, an implantable variable rate activity-based pacemaker detects movements of the patient, discriminates between those detected movements which are related to true physical exercise and those detected movements which arise from forces or causes other than exercise, samples the detected movements related to exercise in successive equal intervals of time to determine whether the exercise is more vigorous or less vigorous than that which occurred during prior time intervals, and adjusts the pacing rate accordingly. In a process according to that invention, the patient's mechanical movements are detected and converted to a signal whose frequency and amplitude vary with rapidity and intensity of the detected movements, the signal is selectively limited to appreciable amplitude values in the frequency range below 4 Hz representing true exercise, maximum and minimum signal amplitude values are detected in each time interval, and the differences thereof are stored, averaged over a predetermined number of consecutive time intervals and compared with the average over a corresponding number of immediately preceding consecutive time intervals.

In the preferred embodiment of the invention claimed in the docket '812 application, the low-pass filtered signal is processed within successive intervals in blocks of time, as a moving window. The difference between the maximum and minimum signal amplitudes in each scanning interval of 300 ms, for example, is calculated and added to corresponding calculations made for previous successive scanning intervals in that block (e.g., the first block). This value is then averaged for that block by dividing it by the number of intervals scanned. If the difference between that average and the average for the second period or block scanned by the moving time window exceeds a predetermined activity baseline related to units of gravity, and if this is confirmed over the next few blocks of time, it is indicative of the commencement or an increase of patient activity. This indicia is then used to trigger an appropriate jump in the pacing rate.

In this way, the activity pacemaker of the docket '812 application exhibits considerably greater sensitivity to changes in patient activity (and, in particular, to changes in workload during true physical exercise) than prior art activity pacers are capable of. It is a principal object of the present invention to use such signal processing technique to ascertain and then to utilize the frequency as well as the amplitude of the activity signal indicative of true exercise.

A related object of the present invention is to use frequency and amplitude values determined from the activity signal to control the pulse rate generated by an implantable pacemaker.

SUMMARY OF THE INVENTION

The present invention takes advantage of the scanning or moving window technique of signal processing described in the '812 application to detect the frequency as well as the amplitude, i.e., both components, of the processed activity-sensed signal (or simply, the activity signal). That is, the signal is processed and calculations are made to obtain information regarding its substantially instantaneous amplitude and frequency by looking at only one basic signal parameter, amplitude. This is achieved in the following manner.

The maximum amplitude and the minimum amplitude of the bandpass (actually, low-pass) signal are detected in each of successive predetermined intervals of time according to the desired scanning window. In the preferred embodiment, a 300 ms scanning interval is used, but the size or "opening" (time interval) of this window should be selected to be less than the period of the likely greatest repetition frequency of the exercise in which the particular patient may be engaged, within limits to be discussed herein. The minimum value and the maximum value of the signal within that interval are detected, and the difference between them is calculated and stored. Alternatively, the difference between the sum of all amplitude maxima and the sum of all amplitude minima in the window may be calculated and stored. This process is repeated for each of the successive 300 ms intervals over a block of time. The difference between these maximum/minimum values is a value A for the first window, a value B for the second window, a value C for the third window, and so forth.

The differences (or difference values) of the samples for the selected windows thereby obtained provide information regarding not only the magnitude of the patient's exercise at any given instant, but also the frequency of the repetitions being undertaken in that exercise, whether it involves walking, running, bicycling or other activity. This is because the difference between the maxima and minima in the window will be increasingly greater with increasingly higher frequencies, even though the absolute value of the signal amplitude may remain the same in successive windows.

An average is taken of the number of successive difference values of max and min amplitudes in the scanning windows (e.g., four values, seven values, or whatever successive number of windows is scanned in a block of time), to provide a mean or average difference value (i.e., [A+B+C+D]/N, where, in this example, N=4). The calculation preferably follows a first-in, first-out basis, in which the difference value E replaces the difference value A in the next calculation of the mean, and so on. This provides the advantages of fast reaction to changes in exercise, allowing changes in the pacing rate to be triggered relatively quickly (within one 300 ms segment or whatever time interval is used for the moving window), and smooths out inconsistent short term noise. The smoothed output is used to control the pacing rate, and the presence of both amplitude and frequency information regarding the nature of the patient's exercise allows that control to be manifested to more closely track the heart rate of a normal healthy person engaged in similar activity, according to a particular selected characteristic curve or related data.

BRIEF DESCRIPTION OF THE DRAWINGS

The above and other objects, aspects, features and advantages of the present invention will become more apparent from a consideration of the ensuing detailed description of a presently preferred embodiment thereof, taken in conjunction with the accompanying drawings, in which:

FIGS. 5a and 5b illustrate the moving window technique for low and higher repetition frequency activities;

DETAILED DESCRIPTION OF THE PREFERRED EMBODIMENT

Figure 1:
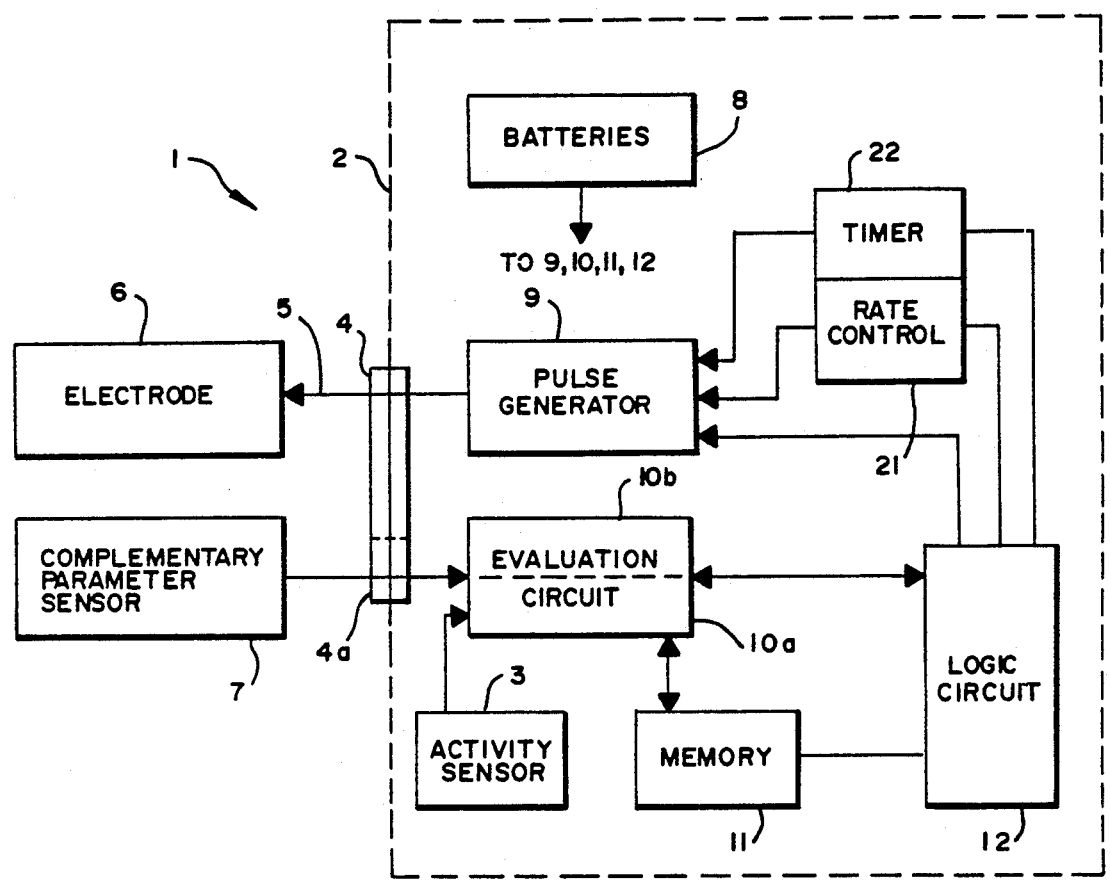
FIG. 1 is a block diagram of a dual sensor cardiac pacemaker which includes activity sensing and control according to the invention.

Referring now to FIG. 1, a cardiac pacemaker 1 includes a case 2 in which the various components are housed, including evaluation circuitry 10a and activity sensor (mechanoelectrical transducer) 3. The circuitry within case 2 is connected via a conventional connector 4 to a pacing lead 5 with a stimulating electrode tip 6. The pacing lead(s), for example, is of the endocardial catheter type for insertion intravenously to position the stimulating electrode(s) relative to excitable myocardial tissue in the appropriate chamber(s) of the right side of the patient's heart. The pacemaker may be arranged in conventional fashion for unipolar or bipolar stimulation, and may include known sensing electrode(s) and processing circuitry therefor as well.

A second sensor 7 may be electrically connected to the pacemaker circuitry via a suitable connector 4a, to detect a complementary physiological parameter, such as the central venous blood temperature, whose value is related to heart rate. Sensor 7 may be a thermistor or other suitable temperature sensing element located in the pacing lead 5, in the manner described in the '573 patent, for sensing the blood temperature in the atrium or ventricle of the right side of the patient's heart.

The implanted pacemaker case 2 further houses a battery 8; a pulse generator 9, whose pulse rate is controllably variable, for generating the stimulating pulses to be delivered to pacing electrode 6 for stimulating the patient's heart; evaluation circuits 10a, 10b for processing and evaluating the signals deriving from activity sensor 3 and temperature sensor 7, respectively; a memory 11 for storing data, such as programmed values in conjunction with a conventional external programmer and other data of the type to be described, including a base-line curve and exercise curves (algorithms) representing heart rate as a function of blood temperature, as set forth in the '573 patent; and a logic circuit 12 for controlling the sampling of signals from the sensors and the rate of the pulse generator.

Figure 2A:
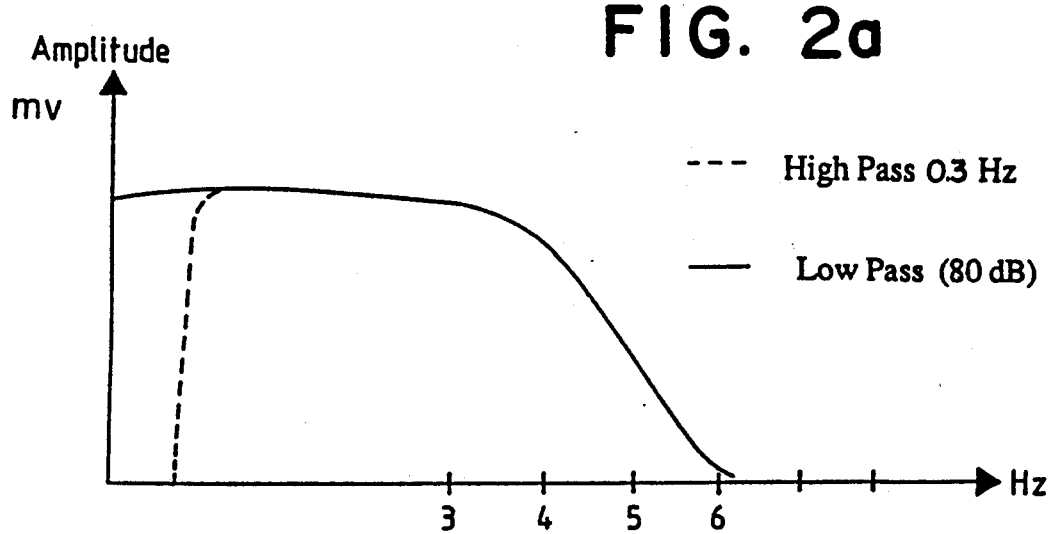
FIG. 2a illustrates the frequency spectrum of the low-pass (bandpass) signals of a mechanoelectrical transducer (activity sensor) used in the pacemaker of FIG 1.

Activity sensor 3 is a small mechanoelectrical transducer, preferably of the type illustrated in FIG. 7 below, which may be fabricated to exhibit an inherent frequency response characteristic in the band below 4 Hz, or is coupled to a filter circuit to pass signals in that preselected band. The frequency spectrum of the bandpassed signals from activity sensor 3 is represented in FIG. 2a, with low pass filtering producing a rapid drop-off at frequencies exceeding 4 Hz, and with high pass filtering to eliminate DC and frequencies below the 0.3 Hz level.

Figure 2B:
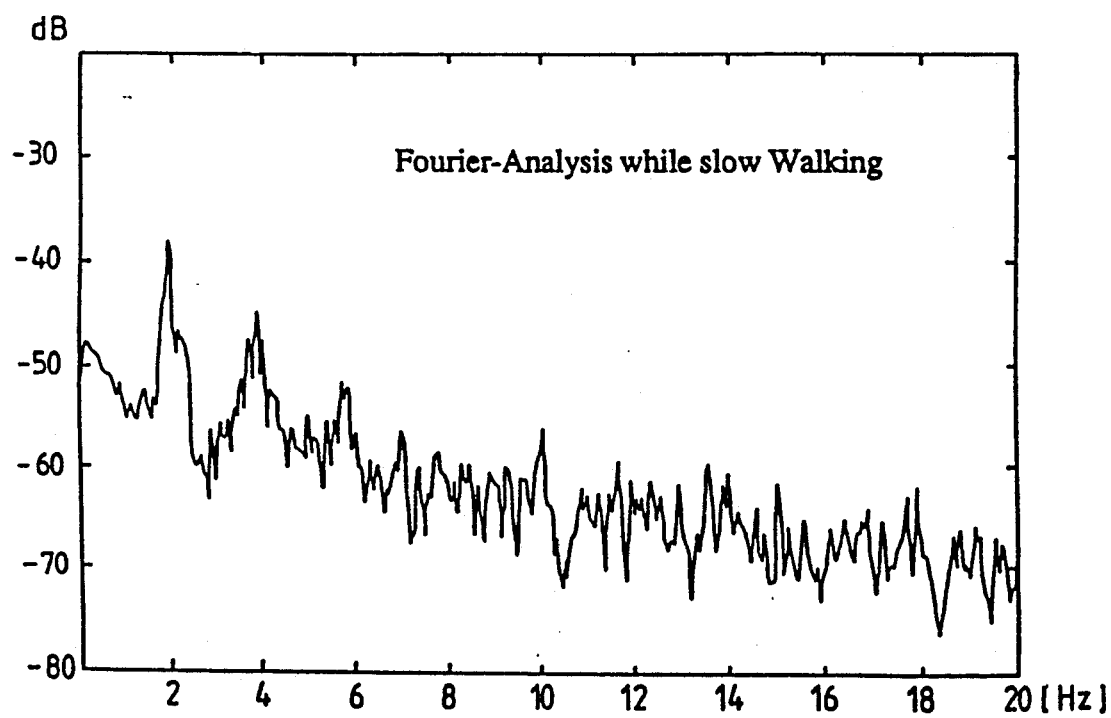
FIG. 2b shows a Fourier analysis with respect to the frequency and amplitude of tee signals from the mechanoelectrical transducer for the activity of slow walking.
Figure 2C:
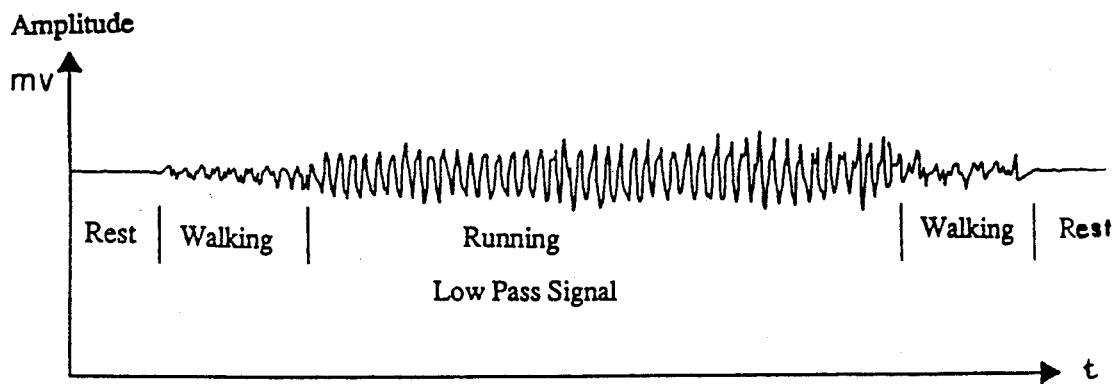
FIGS. 2c through 2f each show frequency and amplitude spectra for different types of activity and disturbances.
Figure 2D:
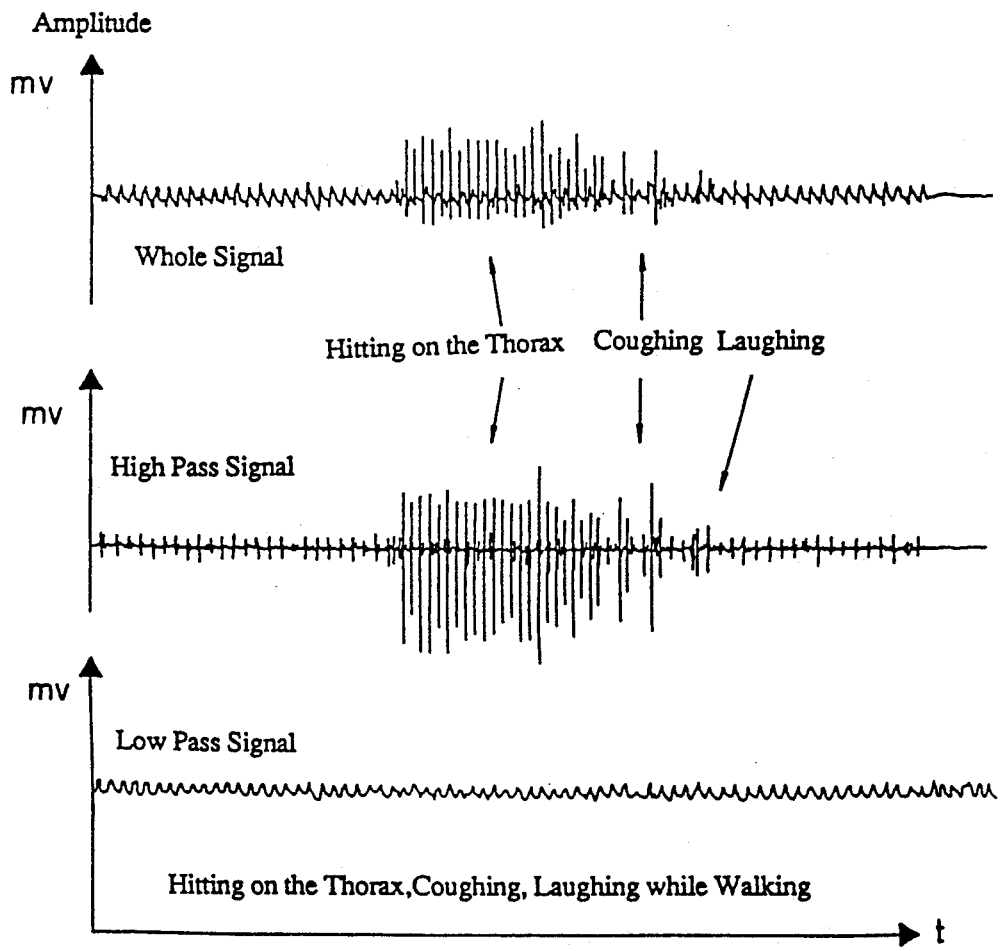

In FIGS. 2b to 2f, the output signals of sensor 3 are analyzed for several different types of activity. FIG. 2b is a Fourier analysis of the processed signals of the activity sensor showing frequency measured in Hz and amplitude measured in db, detected in a slowly walking test subject. FIG. 2c charts the amplitude relative to time of the low-pass signal (i.e., in the band from about 0.3 Hz to 4 Hz) processed from the activity sensor for successive intervals of rest, walking, running, walking and return to rest by the subject. FIG. 2d illustrates, in three separate charts, the unfiltered complete output signal of the activity sensor (upper chart), the high-pass portion (i.e., above the selected band) of the signal (middle chart), and the low-pass portion of the signal (lower chart), detected from a walking subject in which successive intervals of noise are encountered by touching of the pacemaker, coughing and laughing by the subject.

As these Figures indicate, the frequency spectrum for movement of the subject by foot exhibits maximum amplitude at a frequency of approximately 2 Hz and significantly declining signal amplitudes in the range exceeding 4 Hz; an increase in the amplitude of the low-pass activity signal with increasing exercise as the subject goes from walking to running, and an amplitude decrease as the subject returns to walking and ultimately to a state of rest and that the low-pass activity signal is virtually unencumbered by the noise generated from impact on the pulse generator case, coughing, laughing or the like. In contrast, the high-pass signal is significantly affected by noise, so much so that the signal representative of walking is buried in the noise.

Figure 2E:
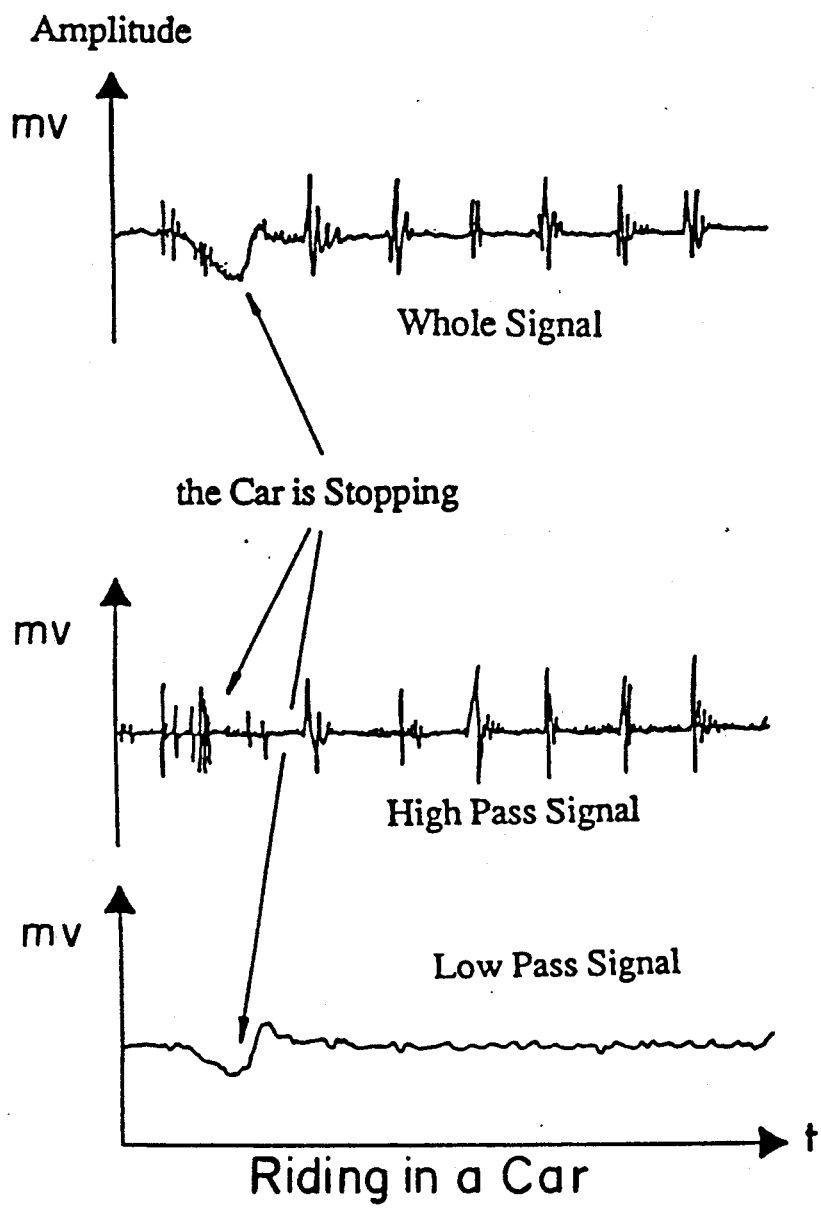
Figure 2F:
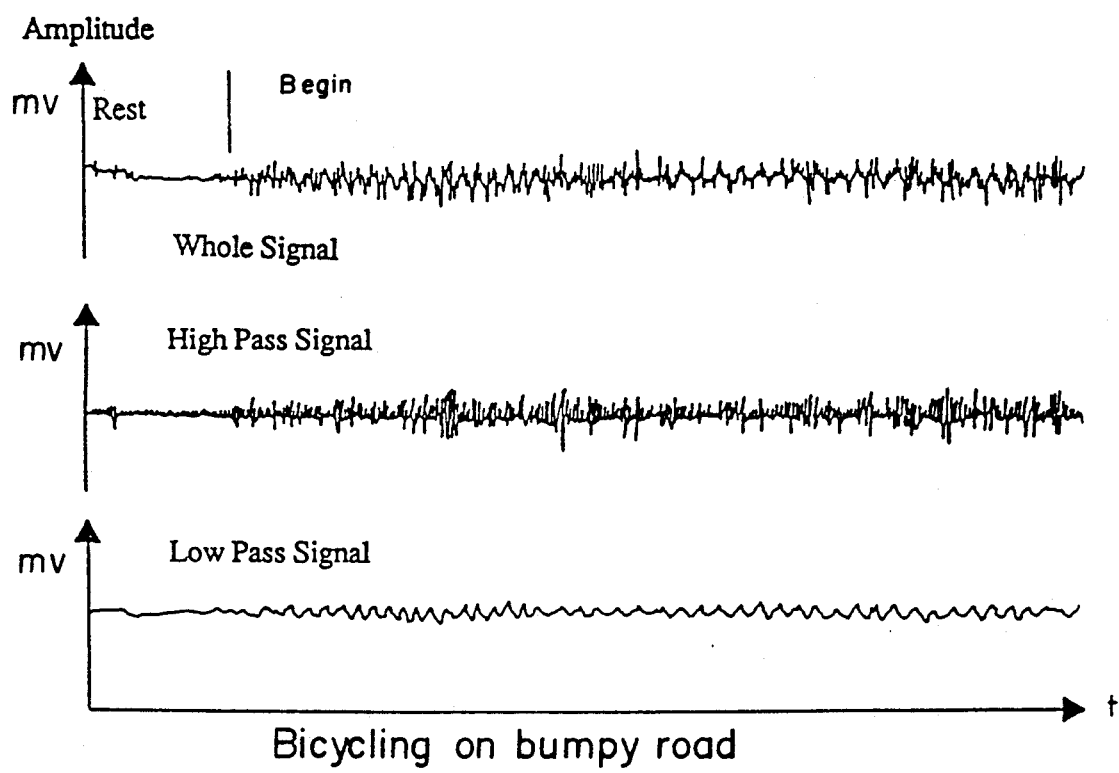

FIGS. 2e and 2f show the signal amplitudes over time for the entire frequency spectrum (upper chart), the high-pass portion (middle chart), and the low-pass portion (lower chart), when the subject is riding in a car and bicycling on an uneven road, respectively Here again, the frequency range below 4 Hz indicates true activity, virtually uninfluenced by any noise peaks. In FIG. 2e, the higher frequency range is replete with noise including spikes at the resonance of the moving car. In FIG. 2f, the noise is also pronounced at the higher frequencies, with a more homogeneous noise distribution attributable to the uneven road surface traversed by the bicycle. In both cases the true activity signal is masked in the high-pass signal.

Figure 3:
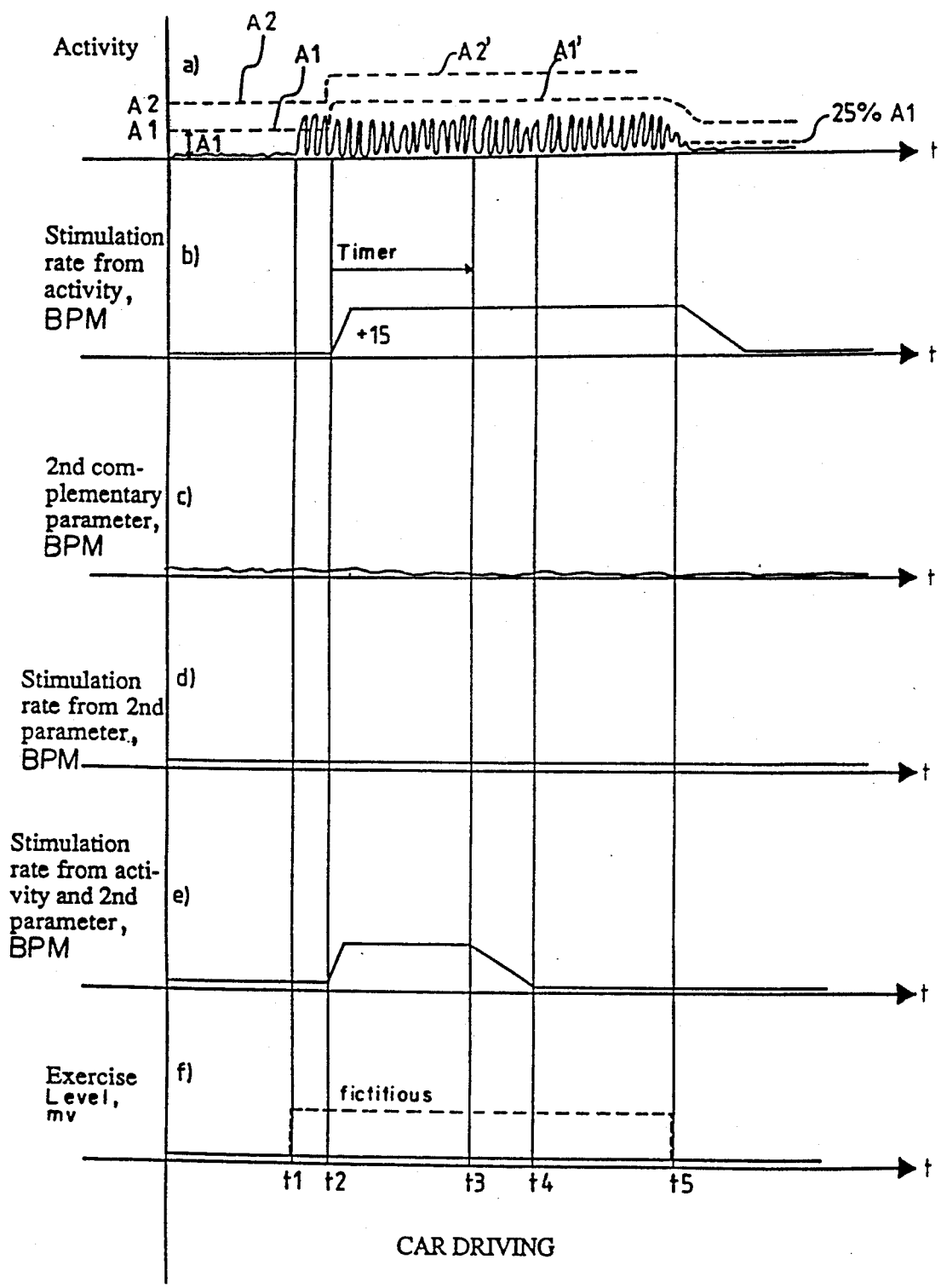
FIGS. 3, 6 and 8 are diagrams of signals developed in a dual sensor pacemaker of FIG. 1 for specified activity.

FIG. 3 illustrates the low-pass activity signal-based pacemaker response when subjected to a false triggering attributable to noise encountered while the patient is riding in a car, for example. Part (f) of FIG. 8 and also of similarly formatted FIG. 6 indicates the nature of the exercise workload. In each of these Figures, the time scale is partly compressed and does not correspond to actual time. For example, the interval between times t1 and t2 is typically less than a minute in duration, whereas some of the subsequent time intervals may be of several minutes to hours in duration each.

In the example of FIG. 3, the "exercise" is fictitious, with the signal detection resulting strictly from noise. Part (a) shows the processed output of activity sensor 3 for the aforesaid low frequency band. Up to time t1 the pacemaker patient is merely sitting in the stationary car; hence, no signal or only small signal variations (attributable to slight movement of the patient in the idling vehicle, for example) are detected At t1, the car starts moving and a higher signal level is detected. It is important to observe that the signal amplitude is exaggerated for the sake of explaining this example; as was observed in FIG. 2e, the low frequency band is quite effective to filter disturbances arising from the moving car.

Figure 4:
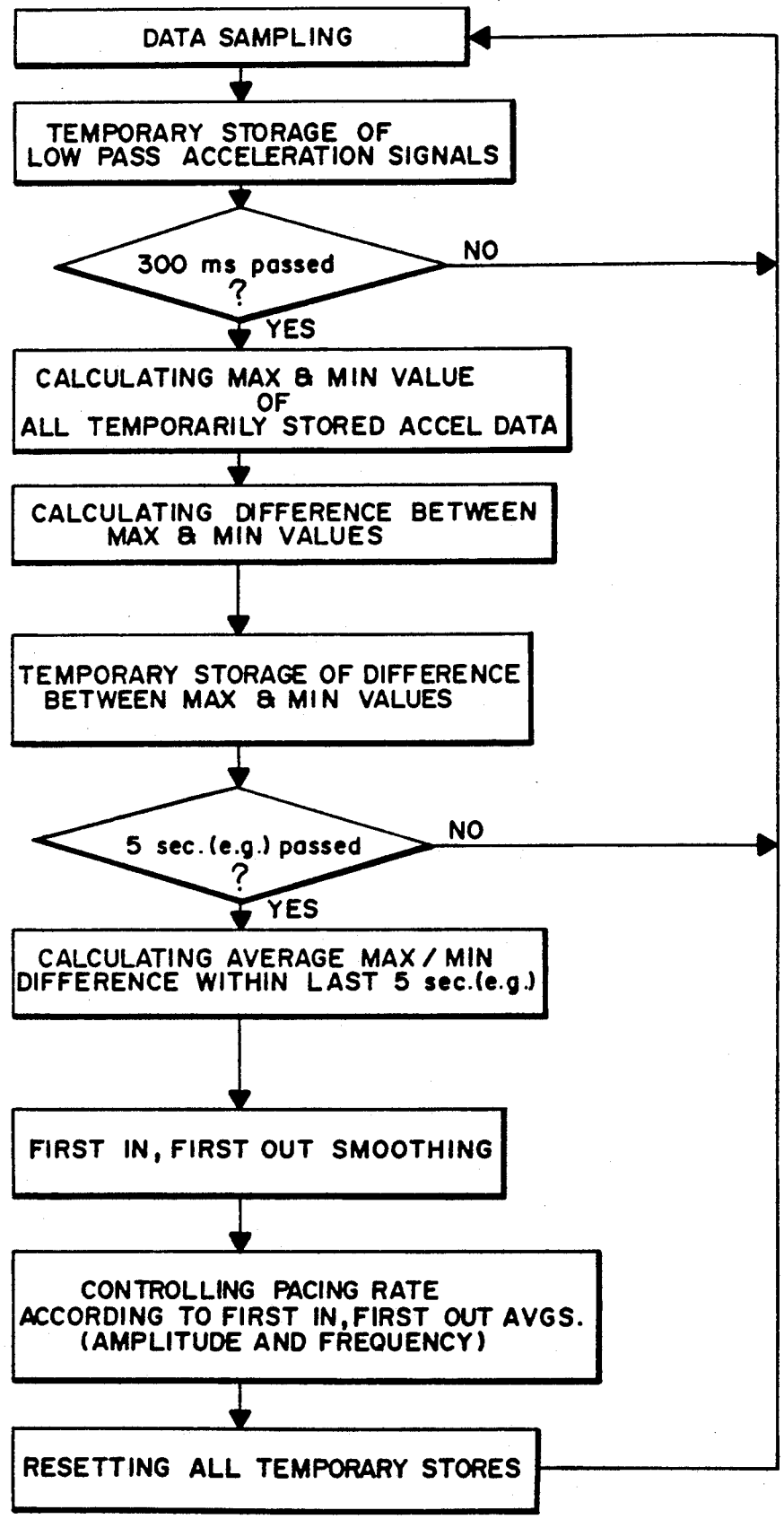
FIG. 4 is a flow chart of activity signal processing in the pacemaker of FIG. 1, according to the invention.

With reference to FIG. 4, the low-pass filtered signal is processed as follows The evaluation circuit 10a processes the signal in successive blocks of time of, say, five seconds each A scanning or moving window is used to detect both amplitude and frequency. The filtered activity signal is sampled at a relatively low sampling rate to conserve the pacemaker battery. The sampled low-passed acceleration (activity) signals are temporarily stored until a preselected (e.g., programmed) time interval has passed. An interval or window of 800 ms has been found empirically to be quite suitable, and is used in the preferred embodiment of the invention. The minimum and maximum values of all temporarily stored acceleration data within this interval are calculated following the sampling and holding over the entire interval. The difference between the maximum value and the minimum value so determined is then calculated and temporarily stored.

At the higher frequencies of the activity signal within the low-pass band of interest, the difference between the maximum and minimum values increases, and so this influences the difference value for any given scanning window. That is, an increase in frequency increases the probability of detecting the real maximum and minimum values within each window, because the same maximum and minimum values at higher frequencies have a relatively greater difference value despite the same absolute values, as may be seen from FIGS. 5a and 6b.

It is important to emphasize, first, that the technique of the present invention is not merely the processing of a signal to find maximum and minimum values and thereby to calculate the signal frequency. Rather, with regard to accelerometer signals or activity signals used for controlling the stimulation rate of a pacemaker pulse generator, the technique of the present invention does not require actual calculation of frequency. A currently popular activity pacemaker relies on the frequency of occurrence of an event—that is how often the event occurs—by looking at zero crossings. An even more complicated approach is taken in another known pacemaker by calculating the integral of the zero crossings. By comparison, the present invention employs a relatively simple means and method to detect the activity signal amplitude and at the same time, or collaterally, to obtain information regarding frequency of the event.

FIGS. 5a and 5b are activity signal waveforms useful for explaining the moving window technique FIG. 5a is the activity signal amplitude over time for a patient exercising (treadmill walking) at a pace (i.e., speed or frequency of steps) of 1.2 Hz, which represents a period of approximately 850 ms. The sum of the max/min difference values obtained for the eight 300 ms intervals in this example is 20.0 cm. In FIG. 5b, the patient is walking at a faster pace—here, 1.5 Hz or a period of 666 ms—and the sum of the max/min deltas over the same eight intervals is 30.2 cm.

It will be observed, then, from a comparison of these two Figures that although the absolute amplitudes may be the same in two blocks of time, the delta or difference between maximum and minimum amplitudes taken over successive equal time intervals in the two blocks may be quite different. This is because the max/min delta is a function of both (i) increasing amplitudes (indicative of more vigorous steps or other exercise) and (ii) the speed or frequency of exercise for the same step intensity. The higher the frequency, therefore, the greater the probability of correctly detecting the true amplitude of exercise within a given repetition cycle of the exercise; provided that the time interval for the moving window is selected to be less than the period of the repetition frequency (cycle) of the exercise.

With this technique, a measure of the frequency of the activity is obtained, as well as amplitude, from only the detection of amplitude Moreover, although this frequency determination is not precise, it is a useful and important contribution, together with amplitude, to control stimulation rate of the pacemaker during patient exercise. It is clear from FIGS. 5a and 5b, for example, that if the patient goes from the exercise pace of the former to the pace of the latter in first-in, first-out smoothing over a moving average of several consecutive intervals, the stimulation rate of the pacemaker will be increased in a rapid, yet simple and effective manner using this control regardless of no change in absolute amplitude, compared to prior art techniques.

Thus, in situations where patient exercise results in an activity signal indicating events (exercise repetitions, such as walking, running, bicycling, etc.) of the same amplitude but different frequency, the stimulation rate of the pacemaker is controlled to have a greater value at the higher frequency.

An optimum interval for use in the moving window technique may be selected for a given patient based on the general nature of his or higher exercise patterns. The selection is made to reasonably assure that the window is less than the period of the likely repetition frequency of the exercise. As noted above, in the preferred embodiment of the present invention a 300 ms interval is selected, that value having found to be optimum for the particular subject population of the experiments.

If one were to look only at the amplitude using a peak level detector, the result would be different. Such a device always detects the absolute peak, samples and holds it, detects the next peak, and so on. That technique provides information on amplitude only, regardless of frequency. But by using appropriately adjusted short segments in which maxima and minima of amplitudes only are detected and subtracted, as with the present invention, information is obtained concerning both amplitude and frequency. Using that information allows control of the pacemaker pulse rate to correspond to both the determined amplitude and frequency, in a simple manner, to most closely simulate the natural heart rate of a healthy individual undergoing similar exercise.

Returning now to FIG. 4, after calculating and storing the maxima/minima differences over the selected block of time, such as from three to five seconds, encompassing a multiplicity of 300 ms intervals, an average delta is calculated to provide a mean (e.g., $[A+B+C+D]/N$, where A, B, C and D are the difference values calculated and stored for successive intervals and $N=4$ is the number of intervals used in the averaging). Then, in the next averaging operation, E which is the difference value obtained for the next successive interval replaces A, on a first-in, first-out basis.

The use of several blocks of first-in, first-out data, such as ABOD, BODE, ODEF, and so forth, provides the capability for relatively fast change of pacing rate appropriate to change in both the vigor or intensity, and the speed of the exercise, within a single 300 ms segment (or whatever time interval is used). The first-in, first-out calculations also serve to smooth out inconsistent short term noise. The heart rate (pacing rate) adjustment may be made from the information obtained in this manner according to a characteristic curve or appropriate data stored in memory and through the influence of logic circuit 12 acting on rate controller 21, timer 22 and pulse generator 9. After the heart rate control is implemented through the pacemaker for this calculation, all of the temporary stores are reset (FIG. 4) in preparation for the next calculation. Although a digital implementation has been described, the pacemaker may alternatively use a corresponding analog implementation.

Referring again to part (a) of FIG. 3, the jump in the filtered activity signal occurs at time t1 (or an instant later depending on the response time of the activity sensor). The differential amplitude information obtained from the processing of the activity signal is compared with predetermined baseline or threshold values of activity A1, A2, and so forth, each of which may be freely programmable and stored in the memory 11. The initial activity thresholds may be selected according to the particular patient and the type of accelerometer (activity sensor) employed for the pacemaker. By way of example, 0.15 g (unit of gravity) was deemed an acceptable level indicative of patient activity for one test subject, using an embodiment of an activity sensor for which that level of movement produced a signal level of about 60 millivolts If the difference amplitude for the first in-first out calculation from the scanning time window exceeds the first threshold A1, the logic circuit 12 controllably initiates an increase in the rate at which stimulating pulses are generated by the pulse generator 9 by an amount of, say, 15 pulses per minute (ppm, equivalent to bpm). If the second threshold A2 were exceeded at t1, the pulse rate would be increased by a greater amount, say, 25 ppm. This rate increase is accomplished as follows. Logic circuit 12 responds to threshold A1 having been exceeded at t1, by initiating at t2 a preset timing function of a rate controller 21 to which it is connected within housing 2, to increase the pacing rate of the pulse generator 9 by 15 bpm. This timing function produces a predetermined transition to the higher pacing rate, as represented in part (b) of FIG. 8. If there is no further significant change in the differential amplitude obtained from the signal processing, this increased stimulation rate will continue in effect. At the same time that the rate increase is initiated, the exceeded activity threshold A1 is designated as the new activity baseline, and a higher activity threshold A1' (and A2', etc.) is set from which to determine additional activity.

At any tIme that the absolute amplitude of the activity signal drops to 25% of the activity threshold which was exceeded to cause the rate increase, the logic circuit initiates a fall-back program through another timing function of rate controller 21 to gradually reduce the stimulation rate of the pulse generator back to a preprogrammed base rate. As shown in FIG. 3(f), the car comes to a stop at t5. The absolute level of the detected activity signal drops to 25% of activity threshold A1 an instant thereafter (FIG. 3(a)), and the pacing rate is decreased commencing at that time (FIG. 3(b)).

Prolonged rate increases from false triggerings of the pacemaker caused by noise in the filtered output of the activity sensor are avoided, even where the noise is present in the low frequency band and is not rejected by the signal processing. To that end, the logic circuit 12 actuates a timer 22 at t2, coincident with the triggering of the rate increase via rate controller 21, to commence timing a predetermined period (FIG. 3(b)) whose duration is preset according to the response time of the selected second complementary parameter to the onset of exercise or to abrupt changes in level of exercise. If blood temperature is the complementary parameter, the period of timer 22 may be set. for example, at two to three minutes. The duration of the timer period is important because if, during that period, the stimulation rate dictated by the complementary parameter exceeds the rate dictated by the activity signal, the latter relinquishes and the former assumes control of the stimulation rate. On the other hand, if the complementary parameter fails to assume such control, this constitutes a lack of confirmation of the activity signal and an indication of no true activity or of insufficient activity to warrant the rate increase. In that case, the logic circuit 12 actuates the rate controller 21 to initiate a rate reduction routine (fallback program) at the end of the period of timer 22.

The blood temperature measured by thermistor 7 over the timer period is represented in FIG. 3(c). Stimulation rate is calculated from the measured blood temperature as described in the '573 patent, and is represented in FIG. 3(d). In this example the "exercise" is fictitious, and consequently the temporal increase, if any, in the blood temperature would be insufficient to produce a stimulation rate other than is commensurate with the baseline resting curve. In fact, there is no substantial change in the blood temperature according to FIG. 3(c), and therefore virtually no change in the rate determined from the blood temperature as shown in FIG. 3(d). Hence, at time t3, when the timer period expires, logic circuit 12 initiates the rate fallback program of rate controller 21 to gradually reduce the stimulation rate of pulse generator 9 to the programmed base rate at t4. This assures that the patient will not be subjected to improper rate increases as a result of false triggerings for more than the relatively short duration of the timer period, rather than experiencing a prolonged rate increase, for example, over a four hour car ride.

If the evaluation of the filtered activity sensor output indicates a reduction in the averaged maxima and minima of the signal by 75% or more to a value of 25% or less of the activity threshold which has just been exceeded, it is assumed that exercise has ceased. At that point, the logic circuit will initiate the fallback program of rate controller 21 to return the pulse rate of pulse generator 9 to the base rate. The various threshold values and the criterion of reduction of below last-exceeded activity threshold may be selected (programmed) according to the individual patient.

Figure 6:
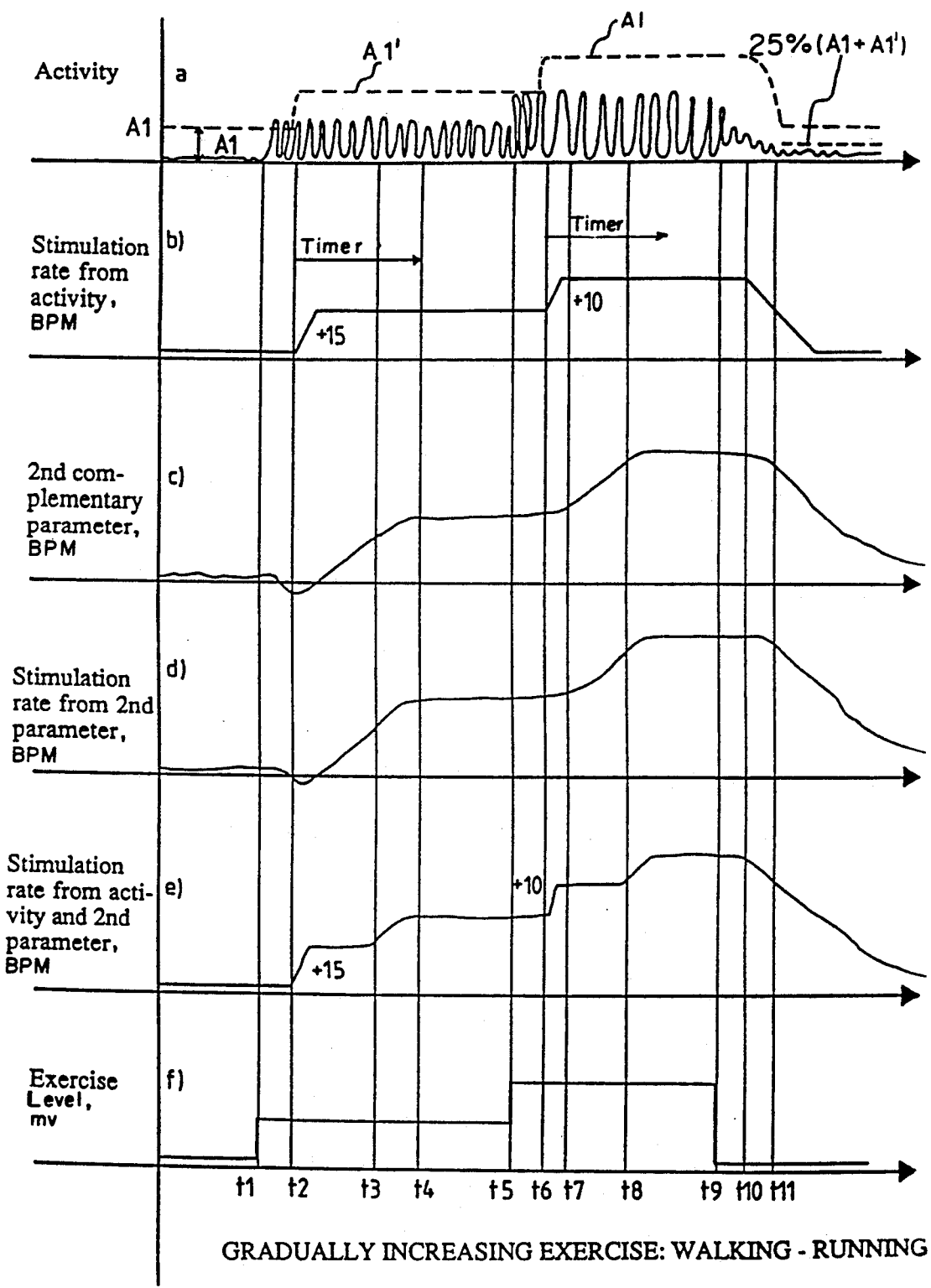

FIG. 6 illustrates the behavior of the pacemaker when the patient undergoes gradual increases of exercise, in the stepped manner shown in part (f). Initially, with the patient at rest, the pacing rate is maintained at the base rate. At t1, the patient begins walking, and, in response to detection of the rhythmical movement, the activity sensor generates a signal which is filtered to pass the frequency band under 4 Hz, shown in part (a). The signal is then processed as described earlier. At time t2, the evaluation circuit determines that the calculated average exceeds activity threshold A1, and, in response, logic circuit 12 increases the stimulation rate by 15 bpm via rate controller 21, and also actuates timer 22 (part (b)). The exceeded threshold A1 is thereupon stored in the memory 11 as the new baseline for activity, and a new higher activity threshold A1' is established (part (a)). The latter is also stored in the memory, along with all other data to be utilized or operated on including base stimulation rate and the current increased rate. As a consequence of the establishment of the new activity baseline A1 and new activity threshold A1', no additional activity will be deemed to have occurred (and thus, no activity signal-induced rate increase will be initiated) until threshold A1' is exceeded by the processed activity signal.

At time t5, the patient goes from walking to running (or from walking at a slow pace to walking at a faster pace, as another example). At time t6 it is determined that the calculated value of the processed activity signal exceeds current activity threshold A1', thereby initiating another increase in the pacing rate, e.g., by 10 bpm (part (b)), the establishment of the now exceeded threshold A1' as the new activity baseline and of a higher level of activity as the new activity threshold A1" (part (a)), and the restart of timer 22 (part (b)). A similar set of events occurs each time the then-current activity threshold is exceeded. In this way, the patient is spared the possibility of prolonged rate increases resulting from false triggerings, but will be subjected to the appropriately higher stimulation rates when actual exercise or a change in exercise level is detected. Put another way, the patient will not experience repeated increases in stimulation rate as the signal level hovers about the same activity threshold, but instead a new higher threshold will be applied upon each rate increase.

At time t9, the patient stops running and againassumes a resting state (part (f)). The cessation of activity is sensed and, at time t10, the calculated value of the processed activity signal has dropped to 25% of the last exceeded threshold A1' (part (a)) which led to the previous double rate increase (initially 15 bpm and then another 10 bpm). In response, the fallback program is initiated for gradual reduction of the stimulation rate toward the base rate (part (b)).

The foregoing discussion of FIG. 6 refers to rate control by the activity signal only. However, as shown in part (c), the blood temperature responds to the onset of exercise at time t1 by dropping slightly and then rising until, at t3, it is at a value determinative of a pacing rate exceeding that of the activity signal-induced rate (part (d)). Since t3 is within the timer period, the stimulation rate control is thenceforth dictated by the sensed blood temperature, commencing from the previously initiated rate increase of 15 bpm above the base rate (part (e)). The blood temperature rises to a steady state value during the first stage of exercise, which is reflected in the combined stimulation rate until time t6, when the aforementioned second activity signal-induced rate increase of 10 bpm occurs. That new stimulation rate is maintained until t8, when the blood temperature-induced rate surpasses this activity signal-induced increased rate within the restarted timer period (part (d). The sensed blood temperature again assumes control of the pacing rate as the temperature continues to rise to a new steady state value during the second stage of exercise.

After the patient stops running at time t9, and this is recognized from the processed activity signal at t10, the combined stimulation rate begins a gradual drop under the control of the fallback program (part (e)), as previously described. At that time, the blood temperature has begun to drop from its relatively high level, and at t11 the temperature commences to drop at a faster pace with a concomitant stimulation rate, but still somewhat slower than the rate according to the fallback program. The sensed blood temperature then again assumes control of the rate reduction toward the base rate. In this manner, it is assured that the pacing rate reduction meets the physiological requirements of the patient to the usual after-effects of heavy exercise, including the body's demand for replenishment of depleted oxygen, which are better accommodated by rate control under the more gradual decrease of the blood temperature. If the patient had stopped exercising before the detected value of the blood temperature had assumed or reassumed control of pacing rate from the activity signal, the stimulation rate would have returned to the base rate strictly according to the fallback program instituted in response to the drop in calclated value of the processed activity signal. However, that would be compatible with the physiological needs of the patient because, in those circumstances, the exercise session would not have extended beyond the relatively short period set by the timer 22.

Figure 7A:
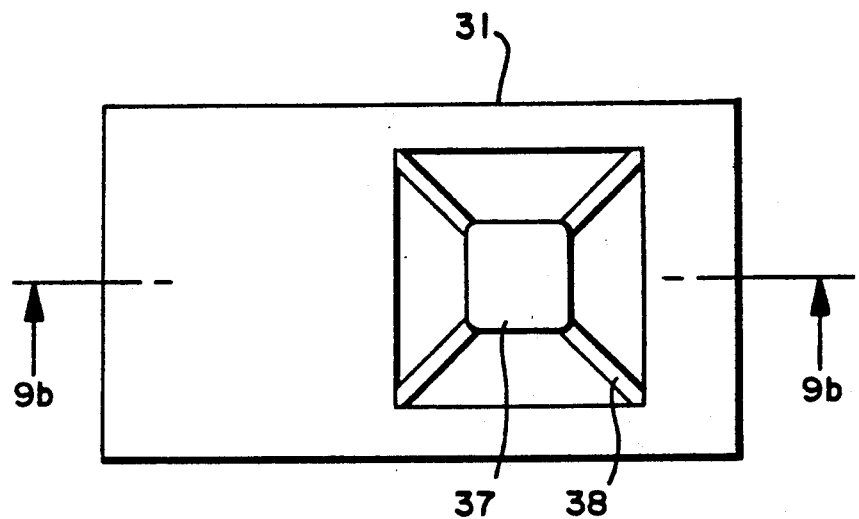
FIGS. 7a and 7b are respectively a front view and a cross-sectional view of a mechanoelectrical transducer which may be used in the pacemaker of FIG. 1.
Figure 7B:
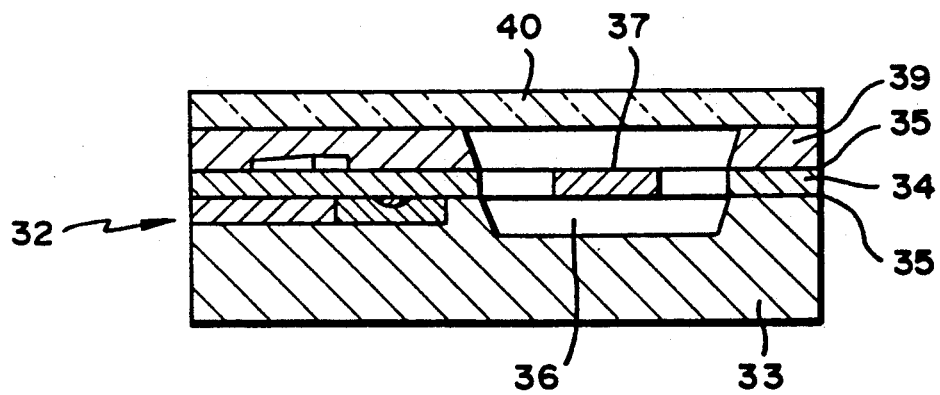

FIGS. 7a and 7b illustrate a mechanoelectrical transducer used in the activity pacemaker. Transducer 31 has an integrated signal filter circuit 32, to provide the proper frequency pass band. The unit 31 comprises a silicon monocrystalline substrate 33 with a 1-0-0 orientation of the crystal planes. A p+ epitaxial conductive layer is formed on the surface of the substrate, followed by a polycrystalline silicon layer 34 sandwiched between passivating layers 35 of silicon dioxide. By anisotropic etching, a cavity 36 is formed in the substrate 33, and portions of layers 34, 35 are removed to form a rectangular plate 37 connected by four arms 38 to the corners of cavity 36. The rectangular plate 37 with arms 38 forms the element responsive to acceleration. A further layer 39 is deposited on the structure, with an opening extending contiguous with the perimeter of cavity 36, to permit axial movement of the rectangular plate on the arms. Finally, a protective layer 40, e.g., a glass plate, is placed over the structure. The integrated circuit 32 for processing the signal generated by movement of the rectangular plate 37 via arms 38 may be fabricated in the silicon layers by conventional semiconductor integrated circuit process technology.

Figure 8A:
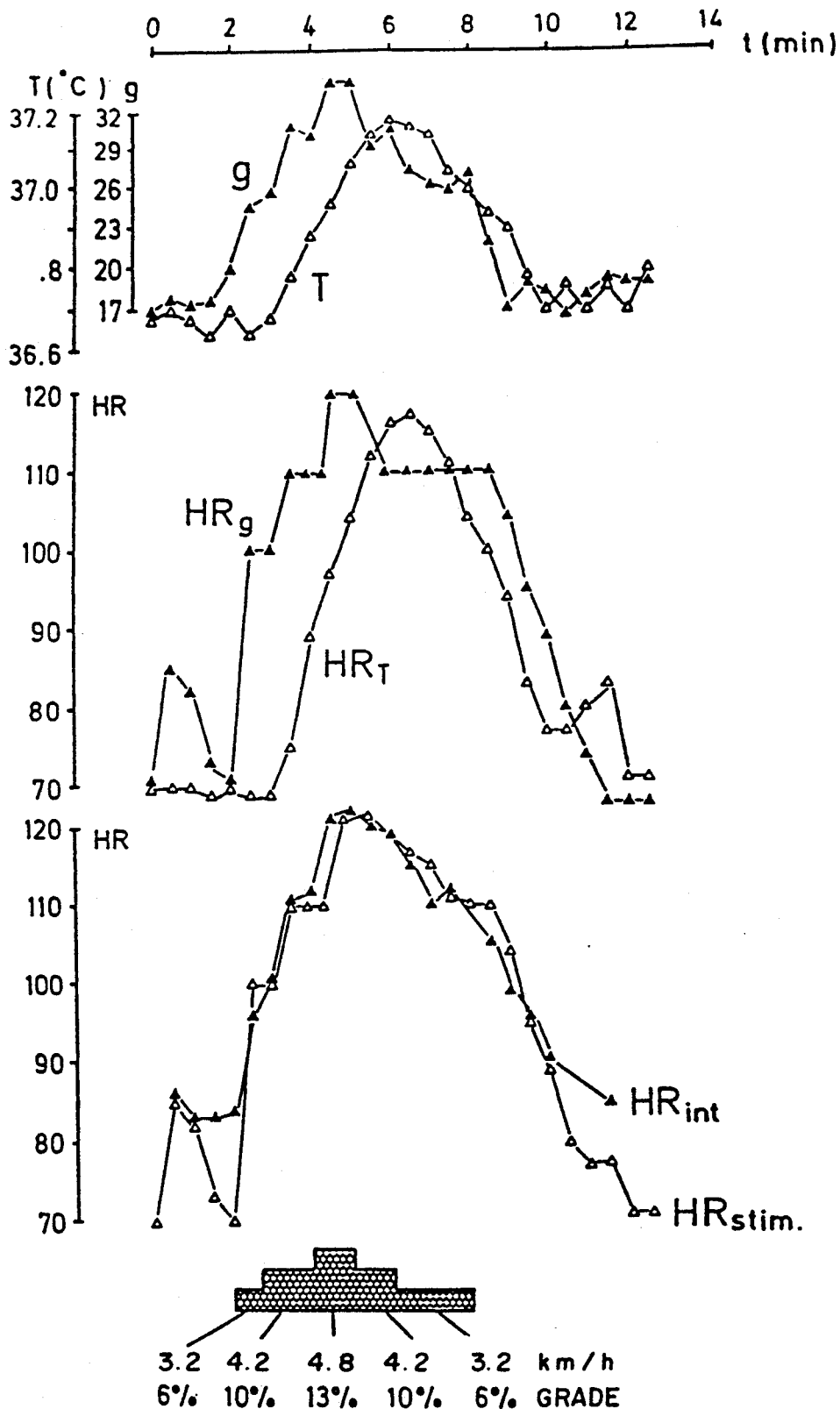
Figure 8B:
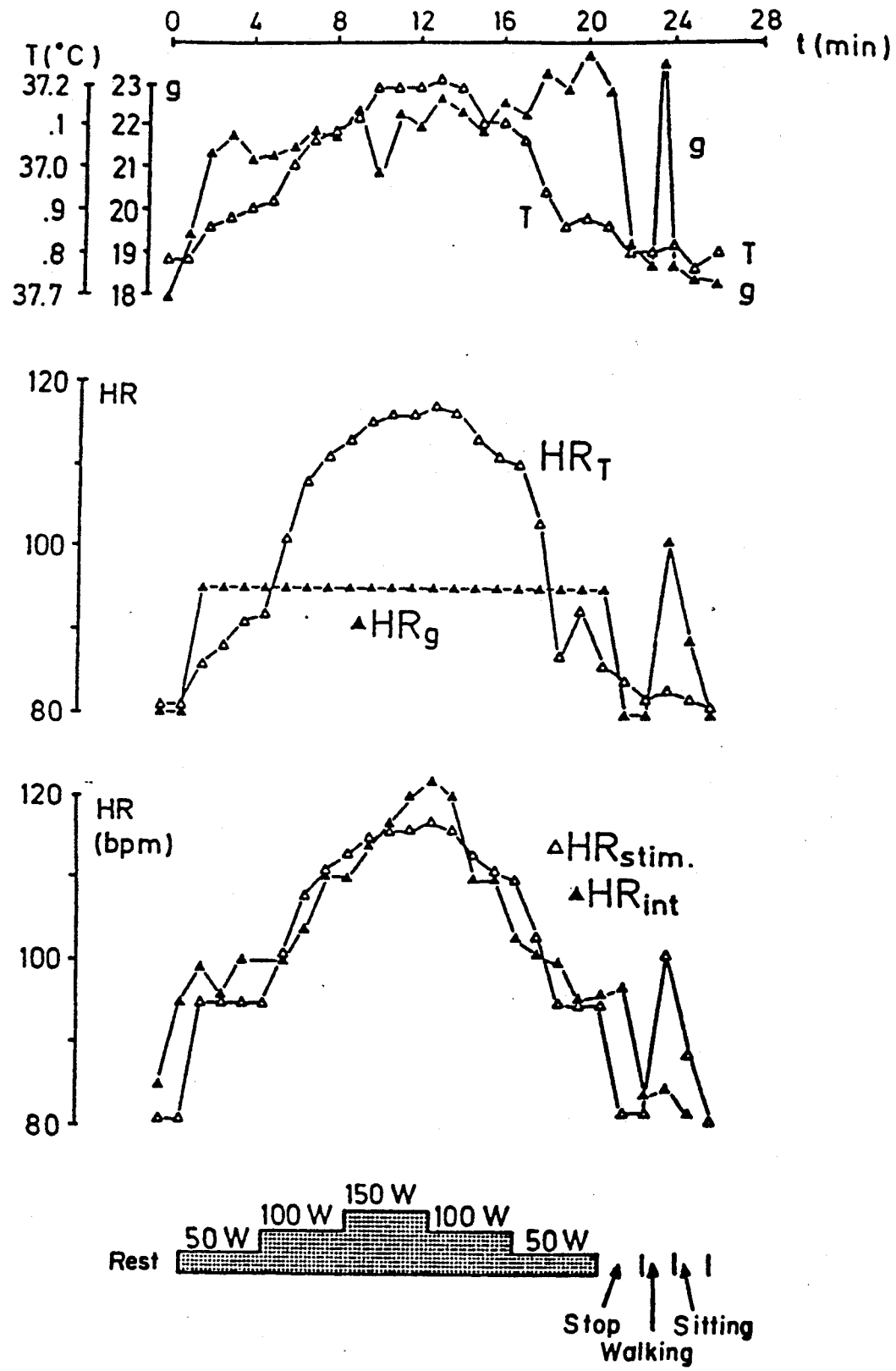

FIGS. 8a and 8b illustrate test results using the dual sensing cardiac pacemaker described above, in which central venous blood temperature of the patient was the complementary parameter. The tests were performed on a healthy person connected to (but not paced by) an external pacemaker otherwise conforming to that described above. The natural (intrinsic) heart rate $HR_{int}$ of the subject while undergoing exercise was recorded on a strip chart and compared to the similarly recorded stimulation rate $HR_{stim}$ generated by the pacemaker pulse generator as controlled by the control system. The "paced heart rate" was detected at the lead connections of the pulse generator.

The upper three diagrams of each of FIGS. 8a and 8b were recorded as a function of time in minutes. The lowermost diagram of each of those Figures (i.e., below the upper three diagrams) is indicative of the exercise regimen performed by the subject, for which the other diagrams of the respective Figure were obtained. The uppermost of the three diagrams of each Figure indicates the measured output of the mechanoelectrical transducer stated in digitized representations into a computer in units g related to gravity (curve g) and the measured values from a blood temperature probe in °C. (curve T). The middle diagram of each Figure shows the heart rate $HR_g$ calculated from and according to the curve g, and $HR_T$ calculated from and according to the curve T, both heart rates being in units of bpm, as calculated independently of each other by the circuitry of the control system. The lower of those three diagrams of each Figure shows a curve of the intrinsic heart rate of the subject (curve $HR_{int}$), and the stimulation rate (curve $HR_{stim}$) as calculated by the control system of the present invention by combining the heart rates $HR_g$ and $HR_T$ according to the principles described above.

In FIG. 8a, the subject underwent a treadmill test in which he was subjected to different speeds and different inclines (grades) by the treadmill. It will be observed that the stimulation rate curve closely matches the natural heart rate curve virtually throughout the test regimen.

In FIG. 8b, the test subject underwent increasing and decreasing exercise on an exercise bicycle. It is interesting to note the increase in curve g in the interval from 16 to 20 minutes despite the decrease in the level of exercise, which is also apparent from the blood temperature curve T. This clearly shows that the test subject was tiring, and moved more on the bicycle notwithstanding that the metabolic expenditure was decreasing. Nevertheless, the curve of stimulation rate constituting a combination of the rates dictated by the activity signals and the sensed blood temperature values in the manner earlier mentioned herein, again closely corresponds to the curve of the appropriate natural heart rate over time.

While a preferred embodiment and process have been disclosed herein, it will be apparent to those skilled in the art from a consideration of the disclosure that variations and modifications of such embodiment and process may be made without departing from the true spirit and scope of the invention. Accordingly, it is intended that the invention shall be limited only to the extent required by the appended claims and the rules and principles of applicable law.

What is claimed is:

1. An implantable variable rate pacemaker adaptive to patient exercise, comprising
   means for detecting movements of the patient,
   means responsive to the detection of such movements for discriminating between those of the detected movements which arise from physical exercise by the patient and those of the detected movements which are unrelated to physical exercise,
   means responsive to such discrimination of the detected movements for generating an electrical signal representative of the detected movements which arise from physical exercise,
   means responsive to said electrical signal for sampling thereof in successive predetermined equal intervals of time to determine from each sample the maximum and minimum values of the amplitude of said signal in each interval, and
   means responsive to such determination of the maximum and minimum values of amplitude for ascertaining therefrom both the magnitude and the relative frequency of the detected movements which arise from physical exercise, to control the rate of said pacemaker according to both the ascertained magnitude and relative frequency.

2. The invention of claim 1, wherein
   the detecting means includes an accelerometer for converting the mechanical movements of the patient to an electrical signal whose frequency and amplitude vary with the rapidity and intensity of the detected movements, and
   the discriminating means includes means for selectively limiting said electrical signal to appreciable amplitude values in a preselected frequency range below 4 Hz.

3. The invention of claim 2, wherein
   the sampling means includes
   means for detecting amplitude maxima and minima of said electrical signal in said preselected frequency range in each of said successive predetermined time intervals,
   means for calculating the difference in value between said maxima and minima in each said interval, and means for determining from said difference the approximate frequency of the detected movements arising from physical exercise.

4. The invention of claim 3, wherein the sampling means includes means for examining said predetermined time intervals at a relatively low sampling rate to conserve energy in said pacemaker.

5. The invention of claim 3, wherein each said time interval is about 300 ms long.

6. The invention of claim 3, wherein the determining means averages multiple ones of the difference values on a first-in, first-out basis.

7. A variable rate pacemaker responsive to patient exercise, comprising
motion sensing means for sensing physical activity of the patient and producing an electrical signal having amplitude maximum and minimum values representative of the repetitions and intensity of said physical activity,
means for detecting said amplitude maximum and minimum values of said electrical signal in each interval of a train of predetermined equal intervals of time, and
means for comparing the difference between the amplitude maximum and minimum values in different ones of said intervals of time to determine the relative repetitions of said physical activity in the compared intervals, for use in controlling the rate of said pacemaker.

8. The invention of claim 7, wherein each of said time intervals is selected to be shorter than the likely shortest interval between repetitions of said physical activity.

9. The invention of claim 8, wherein each said time interval is about 300 milliseconds.

10. The invention of claim 7, wherein the comparing means averages multiple ones of the difference values on a first-in, first-out basis.

11. A process for controlling the heart rate of a patient by artificial stimulation of the heart at a variable rate according to patient exercise, comprising the steps of
detecting movements of the patient,
discriminating between those of the detected movements arising from physical exercise by the patient and other detected movements of the patient, and
scanning the detected movements arising from physical exercise in successive preselected equal intervals of time to assess from amplitude maxima and minima therein the relative rapidity of the physical exercise from one interval to the next, to adjust the stimulation rate according to that relative rapidity.

12. The process of claim 11, wherein said time intervals are preselected to be less than the amount of time likely to be occupied by a cycle of the physical exercise.

13. The process of claim 12, wherein said time intervals are about 300 milliseconds long.

14. The process of claim 11, wherein said scanning includes
ascertaining the difference between the amplitude maximum and the amplitude minimum in each time interval, and
continuously calculating the average of said difference over multiple ones of the time intervals on a first-in, first-out basis to determine the instantaneous frequency of the movements in the physical exercise.

15. A method for controlling the heart rate of a patient by artificial stimulation of the heart at a variable rate according to patient exercise, comprising the steps of
detecting movements of the patient representative of the exercise, and
comparing the maximum and minimum magnitudes of the detected movements in successive equal time intervals to determine therefrom the relative frequency of the physical exercise in said time intervals, for use in controlling the stimulation rate.

16. The method of claim 15, wherein said time intervals are preselected to be shorter than the time period likely to be occupied by each repetition cycle of the physical exercise.

17. The method of claim 16, wherein each of said time intervals is on the order of 300 milliseconds in duration.

18. The method of claim 16, wherein said comparing includes
averaging the difference between the maximum and the minimum magnitude in each time interval over a plurality of the time intervals, and
continuously recalculating said average with each new time interval on a first-in, first-out basis to determine said relative frequency.

19. An implantable activity-sensing, rate adaptive pacemaker for use in a patient, comprising
means for detecting repetitive movements of the patient indicative of true exercise, and
means responsive to detection of such repetitive movements for comparing the maximum and minimum amplitudes of the detected movements in each of successive equal intervals of time to determine therefrom the relative frequency of the repetitions over multiple ones of said time intervals, for use in controlling the stimulation rate of the pacemaker.

20. The invention of claim 19, wherein each of said time intervals is preselected to be shorter than the time period likely to be occupied by each repetition cycle of the physical exercise.

21. The invention of claim 20, wherein each of said time intervals is not greater than approximately 300 milliseconds in duration.

22. The invention of claim 20, wherein said comparing means includes
means for averaging the difference between the maximum and the minimum amplitude in each time interval over a multiplicity of the time intervals, and
means for continuously recalculating said average with each new time interval on a first-in, first-out basis to determine said relative frequency.

23. The invention of claim 19, wherein said comparing means includes
means for averaging the difference between the maximum and the minimum amplitude in each time interval over a multiplicity of the time intervals, and
means for continuously recalculating said average with each new time interval on a first-in, first-out basis to determine said relative frequency.

24. In combination with a sensor for sensing a biological parameter of a patient indicative of the patient's metabolic rate, a variable rate pacemaker adaptive to various hemodynamic conditions, comprising means responsive to the sensing of said biological parameter for producing an electrical signal having amplitude and frequency content representative of changes in said biological parameter, and means responsive to detection of only the amplitude of said electrical signal for determining therefrom both relative amplitude and frequency of said signal representative of changes in said biological parameter for use in controlling the rate of said pacemaker.

25. The invention of claim 24, wherein
the determining means includes
  means for ascertaining the maximum and minimum values of the amplitude of said electrical signal in each interval of a series of predetermined equal intervals of time, and
  means for comparing the difference between the amplitude maximum and minimum values in different ones of said intervals of time to obtain the relative frequency of said signal in the compared intervals.

26. The invention of claim 25, wherein
each time interval is selected to be shorter than the estimated shortest period associated with the frequency of said signal.

27. The invention of claim 25, wherein
the comparing means averages multiple ones of the difference values on a first-in, first-out basis.

28. A method for controlling the heart rate of a patient by artificial stimulation of the heart at a variable rate according to various hemodynamic conditions, comprising the steps of
  detecting a biological parameter of the patient indicative of the patient's present metabolic state,
  converting the detected biological parameter to a signal having an amplitude and frequency content representative of changes in the biological parameter,
  determining the frequency of said signal from only the amplitude of said signal, and
  using both the amplitude of the signal and the frequency determined from the amplitude to control the patient's heart rate.

29. The method of claim 28, wherein
said determining step includes obtaining from the signal amplitude the maximum and minimum magnitude of the detected biological parameter in successive equal time intervals to ascertain therefrom the relative frequency of the changes of the biological parameter in said time intervals.

30. The method of claim 29, wherein
said time intervals are preselected to be shorter than the shortest likely time period for any cycle of said signal frequency.

31. The method of claim 29, wherein
the obtaining step includes
  averaging the difference between the maximum and the minimum magnitude in each time interval over a plurality of the time intervals, and
  continuously recalculating the average with each new time interval on a first-in, first-out basis to determine the relative frequency.

* * * * *